(12) United States Patent
Saul et al.

(10) Patent No.: US 8,921,068 B2
(45) Date of Patent: Dec. 30, 2014

(54) DETECTION OF MICROORGANISMS INVOLVED IN METABOLISM OF ORGANIC ENVIRONMENTAL POLLUTANTS

(71) Applicants: Michael T. Saul, Cincinnati, OH (US); Sergey Gazenko, Mason, OH (US)

(72) Inventors: Michael T. Saul, Cincinnati, OH (US); Sergey Gazenko, Mason, OH (US)

(73) Assignee: CL Solutions, LLC, Norwood, OH (US)

( * ) Notice: Subject to any disclaimer, the term of this patent is extended or adjusted under 35 U.S.C. 154(b) by 68 days.

(21) Appl. No.: 13/869,650

(22) Filed: Apr. 24, 2013

(65) Prior Publication Data
US 2013/0288294 A1    Oct. 31, 2013

Related U.S. Application Data

(60) Provisional application No. 61/640,516, filed on Apr. 30, 2012.

(51) Int. Cl.
*C12Q 1/04* (2006.01)
*C12N 1/20* (2006.01)

(52) U.S. Cl.
CPC  *C12Q 1/045* (2013.01); *C12N 1/20* (2013.01); *C12Q 1/04* (2013.01); *G01N 2333/21* (2013.01)
USPC ........................ 435/34; 435/253.3; 435/253.6

(58) Field of Classification Search
CPC ............ C12Q 1/04; C12Q 1/045; C12Q 1/10; C12Q 1/12; C12Q 1/14; C12N 1/20
See application file for complete search history.

(56) References Cited

U.S. PATENT DOCUMENTS 4,235,964 A * 11/1980 Bochner .......................... 435/34
2009/0068696 A1* 3/2009 Frimodt-Moller .............. 435/19

OTHER PUBLICATIONS

Wahba et al., J. Gen. Microbiol., 1965, 329-342.*
Cetrimide agar, 2009, http://www.neogen.com/Acumedia/pdf/ProdInfo/7688_PI.pdf.*
Pseudomonas agar P, http://www.bd.com/europe/regulatory/Assets/IFU/Difco_BBL/244820.pdf.*
Pseudomonas isolation agar, Apr. 5, 2011, http://www.neogen.com/Acumedia/pdf/ProdInfo/7329_PI.pdf.*
Phillips, Med. Microbiol, 2:9-15, 1968.*
Kaplan and Kitts. Bacterial Succession in a Petroleum Land Treatment Unit. Applied and Environmental Microbiology, vol. 70, No. 3 (2004), pp. 1777, 1785.
Lim. Microbiology (3rd Edition), Kendall/Hunt Publishing Co., Dubuque IA (2003), p. 366 + cover pages (3 pages).

* cited by examiner

*Primary Examiner* — Jennifer McDonald
*Assistant Examiner* — Qing Xu
(74) *Attorney, Agent, or Firm* — Thompson Hine LLP

(57) ABSTRACT

A method and point of use kit to determine under field conditions the presence and/or amount of a selected *Pseudomonas* species capable of bioremediating organic environmental pollutants, such as petroleum hydrocarbons.

10 Claims, 2 Drawing Sheets
(2 of 2 Drawing Sheet(s) Filed in Color)

DETECTION OF MICROORGANISMS INVOLVED IN METABOLISM OF ORGANIC ENVIRONMENTAL POLLUTANTS

This application claims priority to U.S. Provisional Application Ser. No. 61/640,516 filed Apr. 30, 2012, which is expressly incorporated by reference herein in its entirety.

A method and kit to rapidly detect microorganisms that are involved in the metabolism, and hence the removal, of organic environmental pollutants in samples of water and/or soil. The method uses a novel growth medium that is highly selective for *Pseudomonas* species (sp.), microorganisms that are considered to have the highest potential to metabolize, i.e., degrade, environmental pollutants (Kaplan and Kitts, Bacterial Succession in a Petroleum Land Treatment Unit, Applied Environmental Microbiology 70(3) (2004) 1777-1786).

As used herein, environmental pollutants include, but are not limited to, petroleum hydrocarbons including gasoline, diesel fuel, heating fuel, lubricating oil, cutting oil, and constituents of each. As used herein, the growth media may be in any physical form (e.g., solid, substantially solid, liquid, etc.). The method determines the presence, absence, and/or level of *Pseudomonas* sp., which are among the most metabolically diverse organisms (Lim, D. Microbiology, Kendall/Hunt Publishing Co., Dubuque Iowa, 2003, p. 366). This diversity makes them particularly suitable to bioremediate organic environmental pollutants.

The disclosed method identified *Pseudomonas putida*, *Pseudomonas stutzeri*, and *Pseudomonas fluorescens* as indicators of the potential presence of naturally-occurring degradation of petroleum hydrocarbons and other common organic environmental pollutants. In one embodiment, the method is modified by using a selective growth media containing antimicrobials, antibiotics and vital stain to selectively identify specific *Pseudomonas* sp. that are capable of metabolizing petroleum hydrocarbon environmental pollutants. The growth media, antibiotics, and antimicrobials may be varied to selectively identify different *Pseudomonas* sp.

In one embodiment, the method detected the presence of microorganisms that are known to have the capability to metabolize petroleum hydrocarbons. Microorganisms that are capable of metabolizing petroleum hydrocarbons are naturally occurring, and are found as part of the microbial flora at locations where water and/or soil is contaminated by petroleum. Prior to this invention, known methods to detect whether naturally occurring microbial flora contained these microorganisms were expensive, required special equipment, and required trained specialists. The inventive method and media provide a method and a kit for detection of microorganisms capable of metabolizing petroleum hydrocarbons for use, and that were used, under field conditions without specialized equipment or training.

In one embodiment, the method verified the natural presence of petroleum hydrocarbon-degrading microorganisms either inherently present in the water and/or soil samples. In one embodiment, the method verified the presence of petroleum hydrocarbon-degrading microorganisms added to the water and/or soil through bioaugmentation. The disclosed microbes were added to soil and ground water, and samples of soil and ground water were tested for the presence of the disclosed microbes.

In one embodiment, the method determined the presence and/or concentration of environmental pollutant-metabolizing microorganisms without the necessity of incubating the Petri dishes containing the modified growth media at controlled temperatures, or the necessity of using microscopy to identify the microorganisms. The method thus may be used by someone without specialized training or experience in the identification of microorganisms.

In one embodiment, the invention includes procedures for diagnostic testing of samples of water and/or soil for the presence and/or absolute or relative levels of environmental pollutants. In one embodiment, a composition and/or a kit contains novel selective growth media, antibiotics, antimicrobials, and a stain/dye that enhances effectiveness of the detection method. Examples of such novel selective growth media include, but are not limited to, peptic digests of animal tissue, magnesium chloride, potassium sulfate, etc. An example of such a stain/dye includes, but is not limited to, tetrazolium blue chloride. Examples of such antibiotics include, but are not limited to, erythromycin and ampicillin. An example of such an antimicrobial includes, but is not limited to, triclosan.

An example of use of the method follows. A sample of groundwater was placed into a prepared Petri plate containing a novel selective nutrient media that contained peptic digest animal tissue, erythromycin, ampicillin sodium salt, triclosan, and tetrazolium as principal components. The media composition and concentration range of each component is as follows, inclusive of upper and lower range values: peptic digest animal tissue 10 g/L to 30 g/L; magnesium chloride 1 g/L to 2 g/L; potassium sulfate 8 g/L to 12 g/L; erythromycin 0.005 g/L to 0.02 g/L; ampicillin sodium salt 0.005 g/L to 0.02 g/L; triclosan 0.02 g/L to 0.04 g/L; tetrazolium blue chloride 0.2 g/L to 0.5 g/L; optionally agar 12 g/L to 15 g/L; and optionally glycerol. Agar is optional, depending upon whether the media is in solid form or liquid form. Glycerol is optional, depending upon the growth needs of different types of microorganisms. Glycerol is included when the test requires elimination of species of bacteria such as *P. fluorescence, P. stutzeri*, and others.

A sample of soil (100 g) was stirred in a predetermined volume of water (about 1,000 mL) and the resulting composition was placed into a prepared Petri plate (1 mL) that contained the selective nutrient media. The Petri plates were incubated either at room temperature (about 19° C. to about 22° C.) or at higher temperatures (about 20° C. to about 35° C.) until dark violet colonies were visible, indicating growth of these microorganisms and confirming the presence of these hydrocarbon-metabolizing microorganisms. Typically, colonies are visible on this media after about 24 to 48 hours. The number of colonies represent the relative proportion of petroleum hydrocarbon-degrading organisms in the sample.

Use of the media permits reliable detection and enumeration of the microorganisms in order to qualitatively and quantitatively assess or predict the degree of remediation, via microorganism metabolism of environmental pollutants, in the water and/or soil samples.

One embodiment of the invention is a kit for point of use, e.g., field use. The kit contains the prepared media (e.g., in solid form such as solidified agar, in liquid form such as a broth, in Petri plates, in tubes, in or on a test strip or other device, etc.) and instructions for collecting and assessing samples for microorganism metabolism of environmental pollutants in water and/or soil samples. The kit may optionally include other agents or reagents, other devices, e.g., swabs, mixing containers, transfer devices, etc.) to effect use. For example, the kit may contain means such as a device(s) to combine a soil sample with water, and means to transfer known aliquots of the resulting composition to the media. In another embodiment the kit contains means such as a device(s) to transfer aliquots of a liquid sample directly to the media. Other routine methods known in the art such as serial dilutions, sample filtering, etc. may be included in the method and kit.

Detection of petroleum hydrocarbon-degrading microorganisms from among the variety of microorganisms that may be present in a water and/or soil sample is accomplished by promoting selective growth of a range of selective microorganisms, and by eliminating certain microorganisms. In another embodiment, elimination of unwanted organisms is further accomplished by including commercially-available antibiotics, vital dyes/stains, and antibacterial and antifungal agent in the growth media. These substances eliminate unwanted organisms that are not hydrocarbon-degrading organisms.

The invented selective media promoted growth of a narrow range of *Pseudomonas* sp. microorganisms. In one embodiment, the media promoted growth that was limited to only *Pseudomonas putida, Pseudomonas aeruginosa,* and *Pseudomonas cepacia*. In this embodiment, the media contained glycerol, and glycerol eliminated *Pseudomonas stutzeri* and *Pseudomonas fluorescens*. In one embodiment, the media promoted growth that was limited to only *Pseudomonas putida, Pseudomonas aeruginosa, Pseudomonas cepacia, Pseudomonas stutzeri,* and *Pseudomonas fluorescens*.

The following non-limiting examples illustrate embodiments of the inventive method.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

EXAMPLE 1

Figure 1:
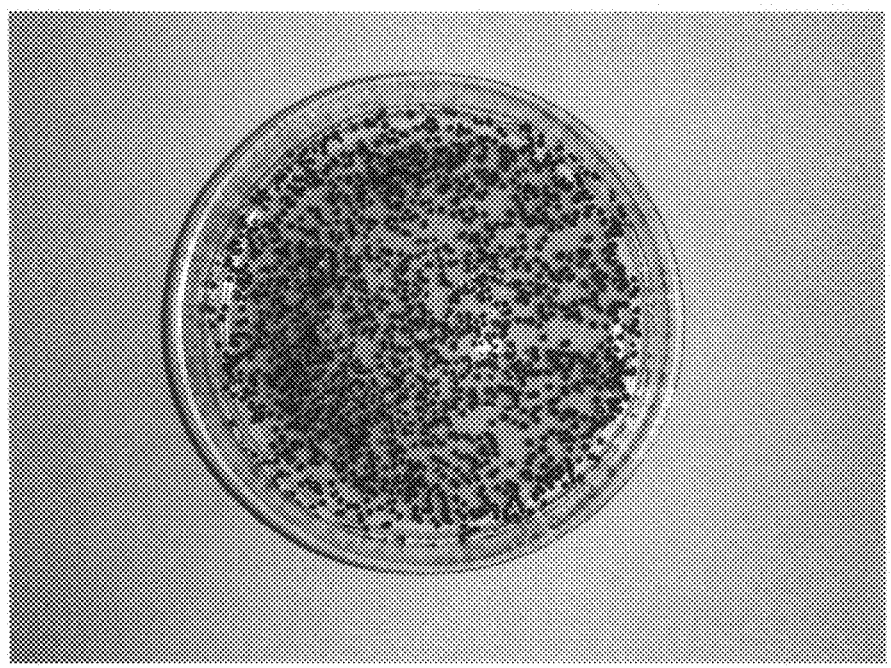
FIG. 1 is a photograph of a Petri plate containing medium showing growth of *Pseudomonas putida*.

As evidence that the media, previously described, supports growth of petroleum-degrading organisms such as the *Pseudomonas* sp. described, one mL of a water solution containing 1,000 *Pseudomonas putida* cells was added to the surface of a Petri plate (1 mL) prepared as described. The Petri dish was sealed and stored at room temperature (about 20° C.). After 48 hours the plate was photographed, as shown in FIG. 1.

The results demonstrated that *Pseudomonas putida* growth on the media occurred. The results verified that the method detected the most common petroleum degrading microbes from a specially prepared solution.

EXAMPLE 2

Example 2 demonstrates use of the inventive kits in the determination of whether bioaugmentation was necessary to establish a population of petroleum-degrading organisms at the location of a petroleum spill.

Figure 2:
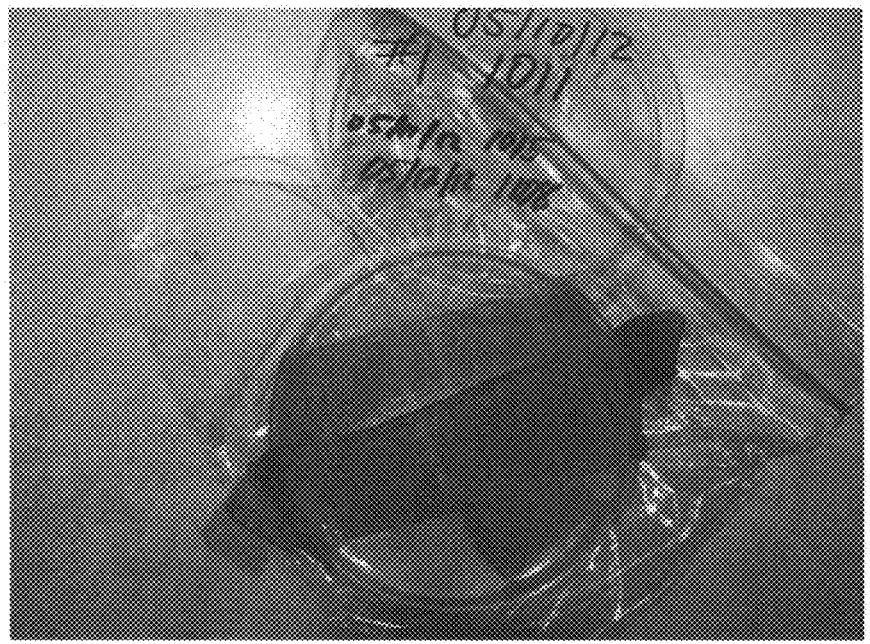
FIG. 2 is a photograph of a Petri plate inoculated with water from the site of a diesel fuel spill.

The inventive kits was used to collect a water sample from the site of a recent railroad diesel fuel spill, and to apply 1 mL to the surface of a Petri plate prepared as previously described. The plate was sealed and then incubated for 48 hours at room temperature (about 20° C.) and then photographed as shown in FIG. 2. The designation #1 refers to the sump where the water samples were obtained. As shown in the following photograph, no petroleum-degrading colonies were seen after 48 h incubation. The lack of growth, in the absence of bioaugmentation, would lead one to conclude that no *Pseudomonas putida* were present in the water sample.

Figure 3:
FIG. 3 is a photograph of a Petri plate inoculated with water from the site of a diesel fuel spill after 30 days bioaugmentation.

Water in the same #1 sump as in Example 1 underwent bioaugmentation treatment for 30 days with petroleum degrading microorganisms using the inventive method. The petroleum degrading organisms were added to the ground water 20 feet to 40 feet from the sample locations. After this 30 day bioaugmentation treatment, a 1 mL aliquot of the same #1 water sample, now treated, was added to the surface of a different Petri plate prepared as previously described. The plate was then sealed and incubated for 48 h at room temperature (about 20° C.) and then photographed as shown in FIG. 3.

Numerous petroleum-degrading colonies were seen. Note that the camera's date was incorrectly set. Comparison of the results of samples from several sumps indicated colony densities that represented the relative proportion of petroleum hydrocarbon-degrading organisms in the sample. Sample #1 showed a greater density of colonies than the other two samples. This comparison is useful in monitoring and planning bioaugmentation using petroleum-degrading microbes.

The embodiments described in the specification are only specific embodiments of the inventors who are skilled in the art and are not limiting. Therefore, various changes, modifications, or alterations to those embodiments may be made without departing from the spirit of the invention or the scope of the following claims.

What is claimed is:

1. A growth medium selective for growth of only *Pseudomonas putida, Pseudomonas aeruginosa, Pseudomonas cepacia, Pseudomonas stutzeri,* and/or *Pseudomonas fluorescens*, the growth medium comprising a peptic digest of animal tissue 10 g/L-30 g/L; magnesium chloride 1 g/L-2 g/L; potassium sulfate 8 g/L-12 g/L; erythromycin 0.005 g/L-0.02 g/L; ampicillin sodium salt 0.005 g/L-0.02 g/L; triclosan 0.02 g/L-0.04 g/L; tetrazolium blue chloride 0.2 g/L-0.5 g/; agar 12 g/L-15 g/L; and excluding glycerol wherein the erythromycin, ampicillin sodium salt, and triclosan are the only antibiotics or antibacterials in the growth medium.

2. A growth medium selective for growth of only *Pseudomonas putida, Pseudomonas aeruginosa,* and *Pseudomonas cepacia*, the growth medium comprising a peptic digest of animal tissue 10 g/L-30 g/L; magnesium chloride 1 g/L-2 g/L; potassium sulfate 8 g/L-12 g/L; erythromycin 0.005 g/L-0.02 g/L; ampicillin sodium salt 0.005 g/L-0.02 g/L; triclosan 0.02 g/L-0.04 g/L; tetrazolium blue chloride 0.2 g/L-0.5 g/; agar 12 g/L-15 g/L; and glycerol wherein the erythromycin, ampicillin sodium salt, and triclosan are the only antibiotics or antibacterials in the growth medium.

3. A point-of-use kit to determine the presence or amount of a *Psuedomonas* species in a potentially contaminated water and/or soil sample, the point-of-use kit comprising
    a container containing the growth medium of claim 1 selective for growth limited to at least one *Pseudomonas* species selected from the group consisting of *Pseudomonas putida, Pseudomonas aeruginosa, Pseudomonas cepacia, Pseudomonas stutzeri, Pseudomonas fluorescens*, and combinations thereof, and a dye or stain, and
    instructions for assessing at least one of the *Psuedomonas* species in the potentially contaminated water and/or soil sample indicating potential for bioremediation of the potentially contaminated water and/or soil sample.

4. The point-of-use kit of claim 3 where the nutrient medium is a solid medium.

5. The point-of-use kit of claim 3 where the nutrient medium is a liquid medium.

6. The point-of-use kit of claim 3 further comprising an implement to manipulate the potentially contaminated water and/or soil sample.

7. A point-of-use kit to determine the presence or amount of a *Psuedomonas* species in a potentially contaminated water and/or soil sample, the point-of-use kit comprising a container containing the growth medium of claim 2 selective for growth limited to at least one *Pseudomonas* species selected from the group consisting of *Pseudomonas putida, Pseudomonas aeruginosa, Pseudomonas cepacia*, and combinations thereof, and a dye or stain, and instructions for assessing at least one of the *Psuedomonas* species in the potentially contaminated water and/or soil sample indicating potential for bioremediation of the potentially contaminated water and/or soil sample.

8. The point-of-use kit of claim 7 where the nutrient medium is a solid medium.

9. The point-of-use kit of claim 7 where the nutrient medium is a liquid medium.

10. The point-of-use kit of claim 7 further comprising an implement to manipulate the potentially contaminated water and/or soil sample.

* * * * *